(12) United States Patent  
Suzuki et al.

(10) Patent No.: US 10,779,809 B2  
(45) Date of Patent: Sep. 22, 2020

(54) METHOD OF LIFTING DISEASED PART, TISSUE LIFTING SYSTEM, AND INDWELLING TOOL

(71) Applicant: OLYMPUS CORPORATION, Tokyo (JP)

(72) Inventors: Takayuki Suzuki, Yokohama (JP); Takeshi Ohdaira, Fukuoka (JP)

(73) Assignee: OLYMPUS CORPORATION, Tokyo (JP)

( * ) Notice: Subject to any disclaimer, the term of this patent is extended or adjusted under 35 U.S.C. 154(b) by 35 days.

(21) Appl. No.: 16/136,595

(22) Filed: Sep. 20, 2018

(65) Prior Publication Data

US 2019/0015090 A1   Jan. 17, 2019

Related U.S. Application Data

(63) Continuation of application No. 11/300,174, filed on Dec. 14, 2005, now abandoned.

(51) Int. Cl.
*A61B 17/02* (2006.01)
*A61B 17/08* (2006.01)
*A61B 17/00* (2006.01)

(52) U.S. Cl.
CPC ...... *A61B 17/0218* (2013.01); *A61B 17/0281* (2013.01); *A61B 17/08* (2013.01); *A61B 2017/00876* (2013.01)

(58) Field of Classification Search
CPC .......... A61B 17/0218; A61B 17/0281
(Continued)

(56) References Cited

U.S. PATENT DOCUMENTS 3,794,041 A  2/1974 Frei et al.
5,593,379 A  1/1997 Rayman
(Continued)

FOREIGN PATENT DOCUMENTS

JP   2004-105247 A   4/2004
JP   2006-271832 A  10/2006
(Continued)

OTHER PUBLICATIONS

Extended European Search Report dated Apr. 17, 2012 in European Patent Application No. 11 00 9241.8.
(Continued)

*Primary Examiner* — Nadia A Mahmood
(74) *Attorney, Agent, or Firm* — Scully, Scott, Murphy & Presser, P.C.

(57) ABSTRACT

A method includes providing an indwelling tool having a magnetic body at the inside of a luminal organ by inserting the tool into a working channel inserted from a natural opening of a living body to the luminal organ, in a manner such that an axis along a length of the magnetic body is arranged substantially parallel to a length direction of the working channel; disposing the tool in a vicinity of a diseased part of the luminal organ; applying a magnetic field to the magnetic body by using a magnetic field generating device provided at the outside of the luminal organ, so as to attract the magnetic body and make a side face of the magnetic body along the axis thereof push against a tissue in the vicinity of the diseased part; and lifting a tissue around a position of the tool, which includes the diseased part, by applying a magnetic force to the magnetic body by using the magnetic field generating device.

2 Claims, 12 Drawing Sheets

(58) Field of Classification Search
USPC .............................................................. 606/1
See application file for complete search history.

(56) References Cited

U.S. PATENT DOCUMENTS

| | | | |
|---|---|---|---|
| 5,595,562 | A | 1/1997 | Grier |
| 5,766,184 | A | 6/1998 | Matsuno et al. |
| 6,171,231 | B1 | 1/2001 | Connolly |
| 6,358,196 | B1 | 3/2002 | Rayman |
| 6,719,768 | B1 | 4/2004 | Cole et al. |
| 2001/0049497 | A1 | 12/2001 | Kalloo et al. |
| 2002/0173805 | A1 | 11/2002 | Matsuno et al. |
| 2004/0050395 | A1* | 3/2004 | Ueda ...................... A61B 34/73 128/899 |
| 2006/0149135 | A1 | 7/2006 | Paz |
| 2007/0004958 | A1 | 1/2007 | Ohdaira et al. |

FOREIGN PATENT DOCUMENTS

| | | |
|---|---|---|
| JP | 2006-280848 A | 10/2006 |
| JP | 2006-280849 A | 10/2006 |
| WO | 2005/002415 A2 | 1/2005 |

OTHER PUBLICATIONS

Partial European Search Report dated Oct. 15, 2007 in European Patent Application No. 07 00 5850.8.

Föll, H., "4.3.6 Hard and Soft Magnets", Electronic Materials, http://www.tf.uni-kiel.de/matwis/amat/elmat_en/kap_4/backbone/r4_3_6.html, dated Jan. 5, 2006, 5 pages.

Office Action dated Jan. 5, 2017 received in U.S. Appl. No. 11/300,174.

Office Action dated Apr. 28, 2015 received in U.S. Appl. No. 11/300,174.

Office Action dated Nov. 17, 2009 received in U.S. Appl. No. 11/300,174.

Office Action dated Jul. 31, 2017 received in U.S. Appl. No. 11/300,174.

Office Action dated Jul. 5, 2016 received in U.S. Appl. No. 11/300,174.

Office Action dated Jan. 14, 2015 received in U.S. Appl. No. 11/300,174.

Office Action dated Oct. 31, 2008 received in U.S. Appl. No. 11/300,174.

* cited by examiner

METHOD OF LIFTING DISEASED PART, TISSUE LIFTING SYSTEM, AND INDWELLING TOOL

CROSS REFERENCE TO RELATED APPLICATION

This application is a continuation application U.S. patent application Ser. No. 11/300,174, filed on Dec. 14, 2005, the entire content of which is incorporated herein by this reference.

FIELD OF THE INVENTION

The present invention relates to a method of lifting a diseased part used in treatment performed in a living body, an indwelling tool used for lifting a diseased part, and a tissue lifting system including the indwelling tool.

DESCRIPTION OF THE RELATED ART

A diseased part produced in a body of a patient is generally removed or cauterized. In a relevant treatment, the body of the patient may be opened in a surgical operation, or an endoscope is inserted from the mouth or the anus of the patient. Japanese Unexamined Patent Application, First Publication No. 2004-105247 (see FIGS. 6 to 11) shows an example of a method of removing a diseased part produced in a luminal organ by using an endoscope. In the method, first, an overtube is inserted into a diseased part of a luminal organ, and then an endoscope is inserted through the overtube. Next, a clip attachment tool is inserted through a channel of the endoscope, and a clip at the head of the clip attachment tool is attached to the diseased part. The endoscope is once pulled out from the overtube, and a magnetic anchor is inserted from the head of the endoscope through the channel. The endoscope is again inserted into the overtube, so as to engage the magnetic anchor with the clip. A magnetic induction member is disposed outside the body of the patient, so that the magnetic anchor is attracted due to magnetic force by the magnetic induction member. The diseased part is pulled via the clip and lifted in the luminal organ. The lifted diseased part is removed using a cutting and removing tool inserted into the channel of the endoscope.

SUMMARY OF THE INVENTION

According to the first aspect of the present invention, a method of lifting a diseased part includes the steps of providing an indwelling tool having a magnetic body at the inside of a luminal organ by inserting the indwelling tool into a working channel which is inserted from a natural opening of a living body to the luminal organ, in a manner such that an axis along a length of the magnetic body is arranged substantially parallel to a length direction of the working channel; disposing the indwelling tool in a vicinity of the diseased part produced in the luminal organ; applying a magnetic field to the magnetic body by using a magnetic field generating device which is provided at the outside of the luminal organ, so as to attract the magnetic body and make a side face of the magnetic body along the axis thereof push against a tissue in the vicinity of the diseased part; and lifting a tissue around a position of the indwelling tool, which includes the diseased part, by applying a magnetic force to the magnetic body by using the magnetic field generating device.

According to the second aspect of the present invention, a tissue lifting system includes an indwelling tool having an anchor fit to the inside of a luminal organ of a living body, and a magnetic body having an elongated shape, which is divided into two magnetized polar parts on either end along a longitudinal axis of the magnetic body; and a magnetic force generating device which is provided at the outside of the luminal organ and has a magnetic body having two poles arranged on an end thereof toward the luminal organ, wherein said two poles correspond to said either end of the magnetic body of the indwelling tool.

According to the third aspect of the present invention, an indwelling tool includes an anchor fit to the inside of a luminal organ; and a soft magnetic body which is magnetized when being exposed in a magnetic field, wherein the soft magnetic body has a side face along a longitudinal axis of the soft magnetic body, the side face being pushed against a tissue inside the luminal organ, and a non-magnetic material is attached to either end of the magnetic body along the longitudinal axis.

PREFERRED EMBODIMENTS

Preferred embodiments of the present invention will be explained below. In the embodiments, common structural elements are given identical reference numerals or symbols, and duplicate explanations are omitted.

First Embodiment

Figure 1:
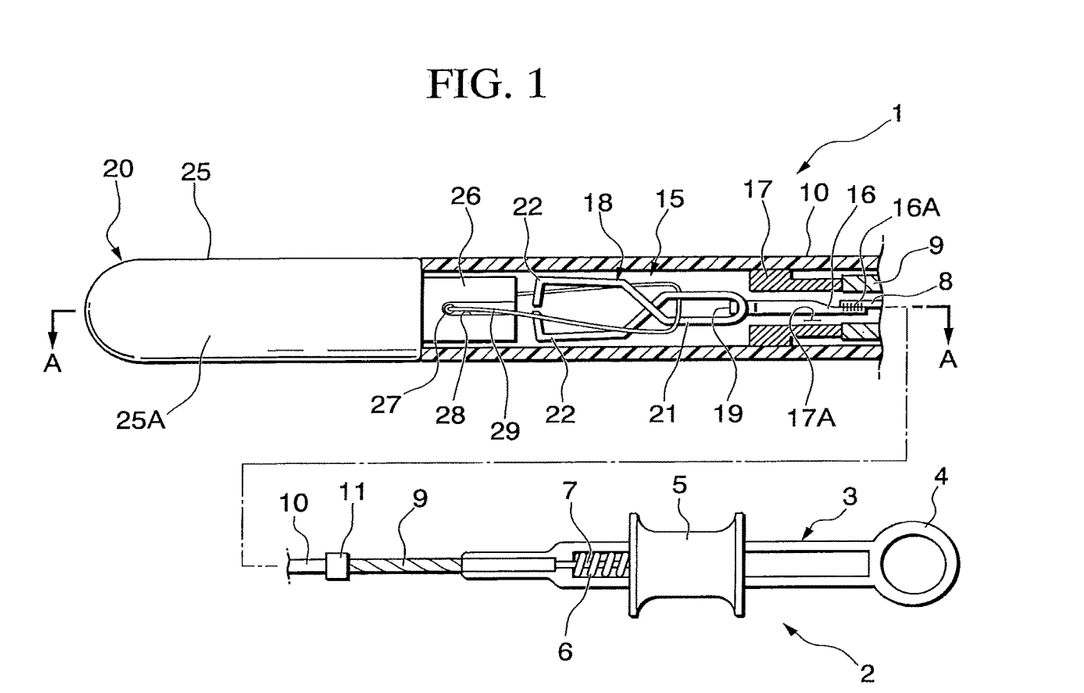
FIG. 1 is a partially sectional view showing the structure of an indwelling tool and an indwelling device as an embodiment in accordance with the present invention.

FIG. 1 shows an indwelling tool and an indwelling device used in a first embodiment. The indwelling device 1 has an operation section 2 handled by an operator. At a base end of a main body 3 of the operation section 2, a ring 4 for a finger of the operator is provided. A slider 5 is attached to the main body 3 in a manner such that the slider 5 can freely slide. The slider 5 is forced toward an end by a compressive-type coil spring 6. A pipe 7 is connected to the slider 5, and a wire is inserted through the pipe 7. This wire passes through a coil sheath 9 which is fixed on the head side of the main body 3, in a manner such that the wire can be freely advanced or withdrawn. The coil sheath 9 passes through an insertion pipe 10 in a manner such that the coil sheath 9 can freely advance or withdraw. The insertion pipe 10 is made of plastic such as fluororesin or polyethylene resin. At a base end of the insertion pipe 10, a grip 11 is provided, which is held by the operator. The insertion pipe 10 and the coil sheath 9 are each long and flexible, and are inserted into a working channel of an endoscope (not shown). The wire 8 extending through the coil sheath 9 is fastened to the slider 5. A connection plate 16 for an indwelling tool 15 is welded to the head of the wire 8.

Figure 2:
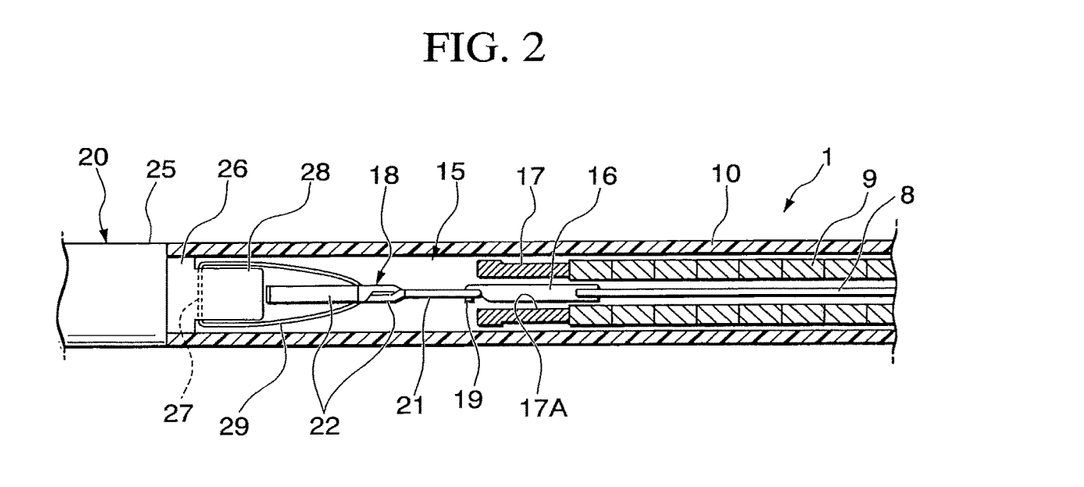
FIG. 2 is a sectional view along line A-A in FIG. 1.

As shown in FIGS. 1 and 2, the indwelling tool 15 consists of the connection plate 16, a tube 17, a clip (or anchor) 18 and a magnetic body 20. The connection plate 16 is welded to the wire 8, so that the connection plate 16 passes through the tube 17 and is pulled out from the head of the tube 17. A hook 19 is formed at the head of the connection plate 16, and a loop portion 21 of the clip 18 is engaged with the hook 19. The clip 18 is made of a thin and long member, a center portion of which is twisted so as to form the loop portion 21. In a natural state, a pair of arms 22 are open toward the head side.

The magnetic body 20 has a main body 25 whose base end forms a holding portion 26 having a smaller outer diameter. The outer diameter of the main body 25 is larger than the inner diameter of the insertion pipe 10, and substantially the same as the outer diameter of the insertion pipe 10. The holding portion 26 is loosely fit to the inner periphery of the insertion pipe 10 by press fitting or the like. The (longitudinal) axis of the magnetic body 20 is sufficiently longer than the diameter thereof. The axis of the magnetic body 20 substantially coincides with the length direction of a head portion of the indwelling device 1. A magnetic body (or material) is made either of a soft magnetic body or a hard magnetic body. In the present embodiment, the magnetic body 20 is made of a hard magnetic material.

Figure 3:
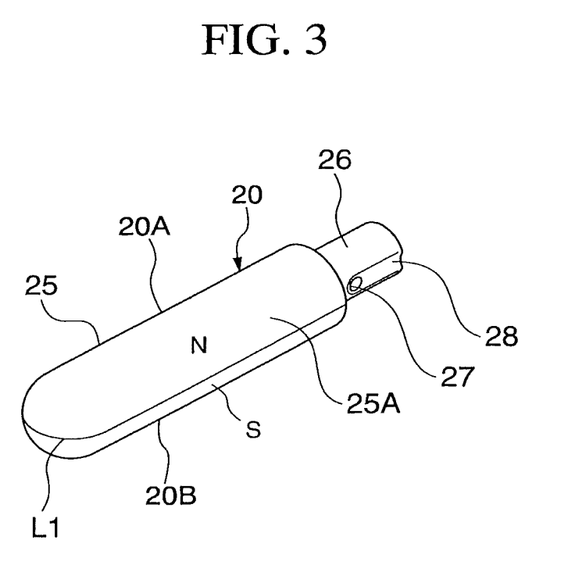
FIG. 3 is an enlarged view of a magnetic body.

As shown in an enlarged view of FIG. 3, the magnetic body 20 is divided into two magnetized polar parts with respect to a plane (as a boundary) positioned parallel to the axis of the magnetic body 20: one is a part 20A as an N pole, and the other is a part 20B as an S pole. A boundary line L1 between the poles matches the position of the axis of the magnetic body 20; however, the boundary line L1 may be offset from the position of the axis of the magnetic body 20.

As shown in FIG. 1, the holding portion 26 has a through hole 27 arranged substantially perpendicularly to the axis of the holding portion 26, wherein a groove 28, which includes the opening of the through hole 27, is formed toward the base end of the holding portion 26. A wire 29 is inserted through the through hole 27 and passes through the groove 28, and further passes inside the loop portion 21 of the clip 18, so as to form a circular shape.

Figure 4:
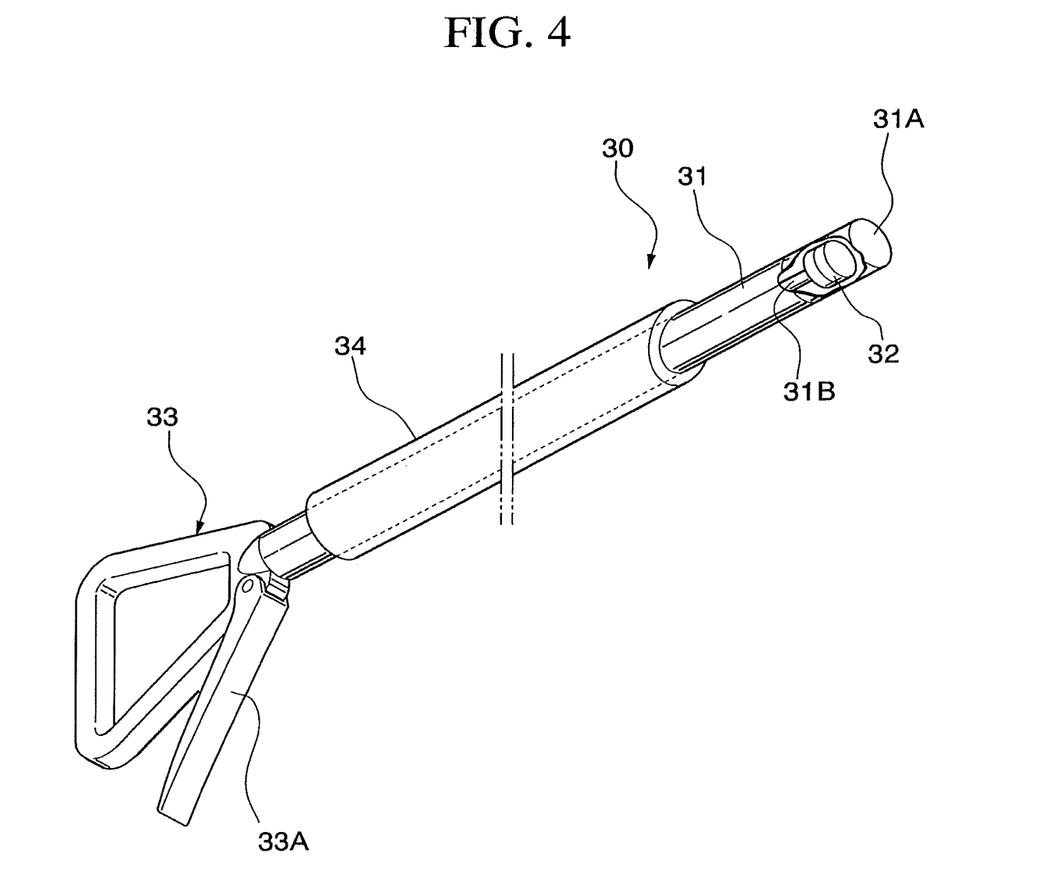
FIG. 4 is a perspective view showing magnetic forceps.

FIG. 4 shows magnetic forceps used in the present embodiment. Magnetic forceps 30 as a magnetic force generating device have a pipe-shaped insertion portion 31 whose head portion is closed by a cover 31A. A pusher rod 31B is inserted into the insertion portion 31, and a magnet 32 is fastened to the head of the pusher rod 31B. At the base end of the insertion portion 31, an operation section 33 is provided. The magnet 32 in the insertion portion 31 can be approached toward or withdrawn from the cover 31A by operating a lever 33A of the operation section 33. The insertion portion 31 passes through a cylindrical sheath 34 made of a hard material. Detailed explanations of the structure and the method of using the magnetic forceps 30 are disclosed in U.S. patent application Ser. No. 11/076,662, related to the applicant of the present Patent Application, where the contents disclosed in U.S. patent application Ser. No. 11/076,662 are incorporated in the present embodiment.

The operation of the present embodiment will be explained.

Figure 5:
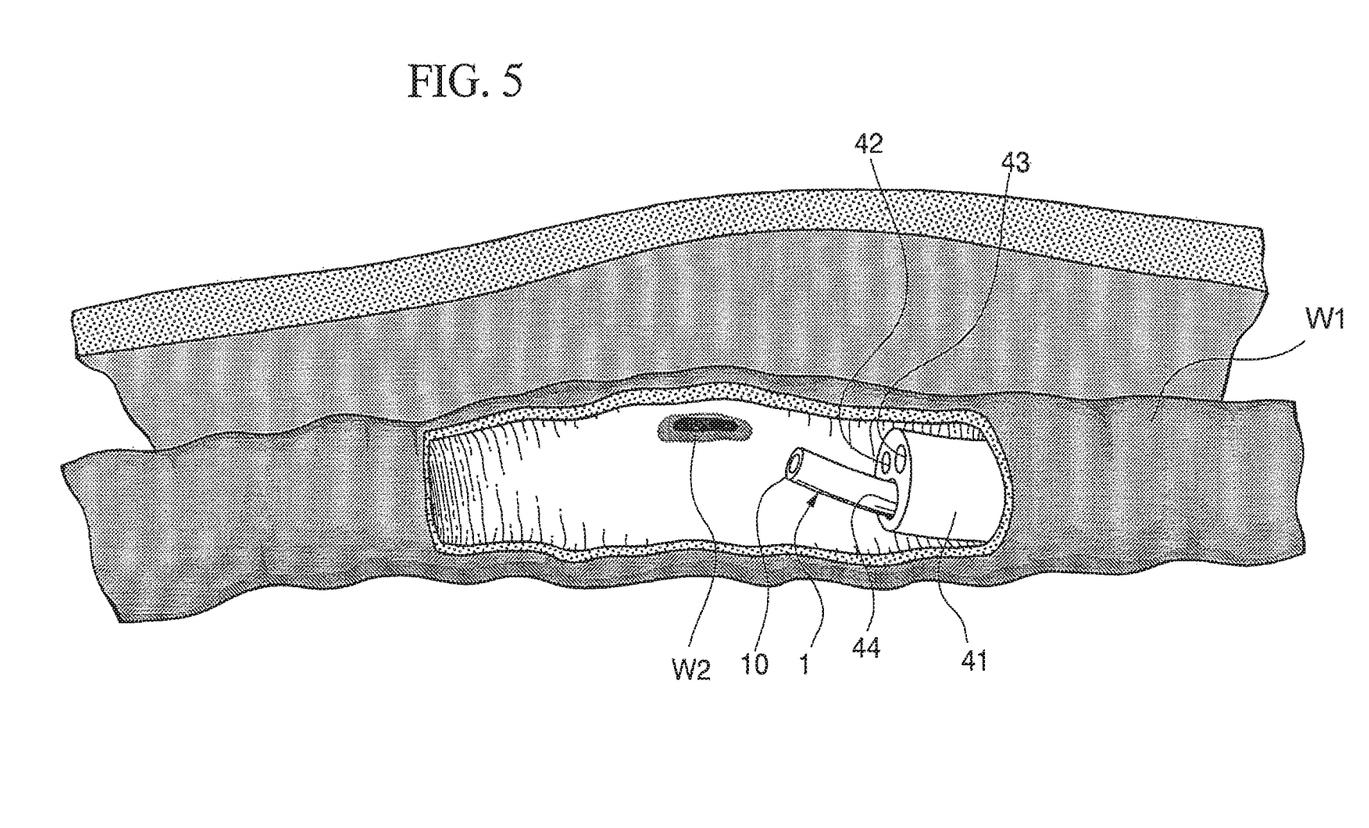
FIG. 5 is a diagram showing a state in which an endoscope is inserted into a luminal organ.

As shown in FIG. 5, an endoscope 41 is inserted from a natural opening (e.g., a mouth, an anus, a nose, or an ear) of a living body into a luminal organ W1. The inside of the luminal organ W1 is observed using an illumination device 42 and an observation device 43 which are provided at the head of the endoscope 41, so as to confirm a diseased part W2 produced inside the luminal organ W1. The indwelling device 1, to which the indwelling tool 15 (used first) is attached, is inserted through a working channel 44 of the endoscope 41. Here, the head of the indwelling device 1 is inserted along the axis (i.e., the length) of the working channel 44. Therefore, the magnetic body 20 of the indwelling tool 15 is inserted in a manner such that the axis of the magnetic body 20 is in parallel with the axes of the working channel 44 and the endoscope 41.

Figure 6:
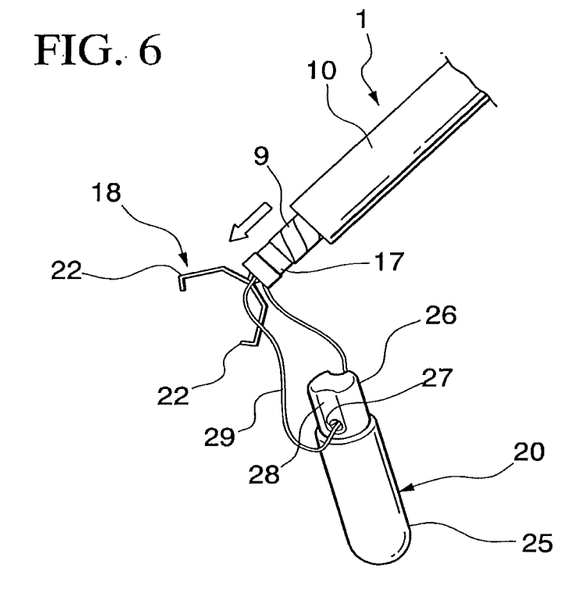
FIG. 6 is a diagram showing a state in which an indwelling tool is made to protrude from an insertion pipe and a magnetic body is hung from a clip.

Then, the grip 11 (shown in FIG. 1) of the indwelling device 1 is held so as to fix the insertion portion 10 and push the operating section 2, so that the coil sheath 9 and the indwelling tool 15 protrude from the head opening of the insertion pipe 10. The clip 18 is directed to a tissue in the vicinity of the diseased part W2 of the luminal organ W1, so as to secure a specific distance between the diseased part W2 and the clip 18. As shown in FIG. 6, the clip 18 proceeds together with the coil sheath 9 so as to push out the magnetic body 20 from the insertion pipe 10. The magnetic body 20 and the clip 18 are coupled with each other via the wire 29; thus, the magnetic body 20 does not fall.

Figure 7:
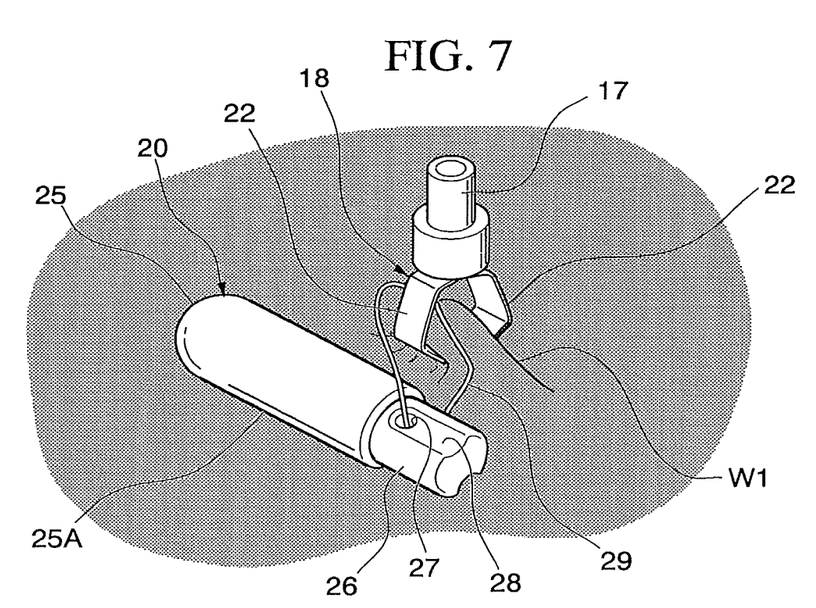
FIG. 7 is a diagram showing the indwelling tool is anchored.

The clip 18 is directed to a tissue in the vicinity of the diseased part W2 of the luminal organ W1, so as to secure a specific distance between the diseased part W2 and the clip 18. When the slider 5 is pulled, the wire 8 pulls the connection plate 16, and the loop portion 21 is drawn into an inner hole 17A of the tube 17, so that the pair of arms 22 open. While the arms 22 are open, the clip 18 is pushed onto a tissue at the indwelling position. When the slider 5 is pulled, the loop portion 21 is drawn into the tube 17, and the arms 22 are pushed onto an end of the tube 17, so that the clip 18 closes and a living tissue is clipped between the arms 22 of the clip 18. When the slider 5 is further pulled, the bending portion of the hook 19 formed at the head of the connection plate 16 is finally released and linearlized, so that engagement between the connection plate 16 and the loop portion 21 is released and the indwelling tool 15 is isolated from the indwelling device 1. When the coil sheath 9 and the insertion pipe 10 are withdrawn, the indwelling tool 15, which clips the tissue, stays and indwells as shown in FIG. 7. The magnetic body 20 is present in the vicinity of the clip 18 via the wire 29. Here, the clip 18, fit to the tube 17, keeps the closed state. Another method of connecting the indwelling tool 15 and the wire 8, and more detailed description for the indwelling process are disclosed in US Patent Application Publication, No. US2002/0173805A1, related to the Applicant of the present Patent Application. The contents disclosed in US2002/0173805A1 are incorporated into the present embodiment.

Figure 8:
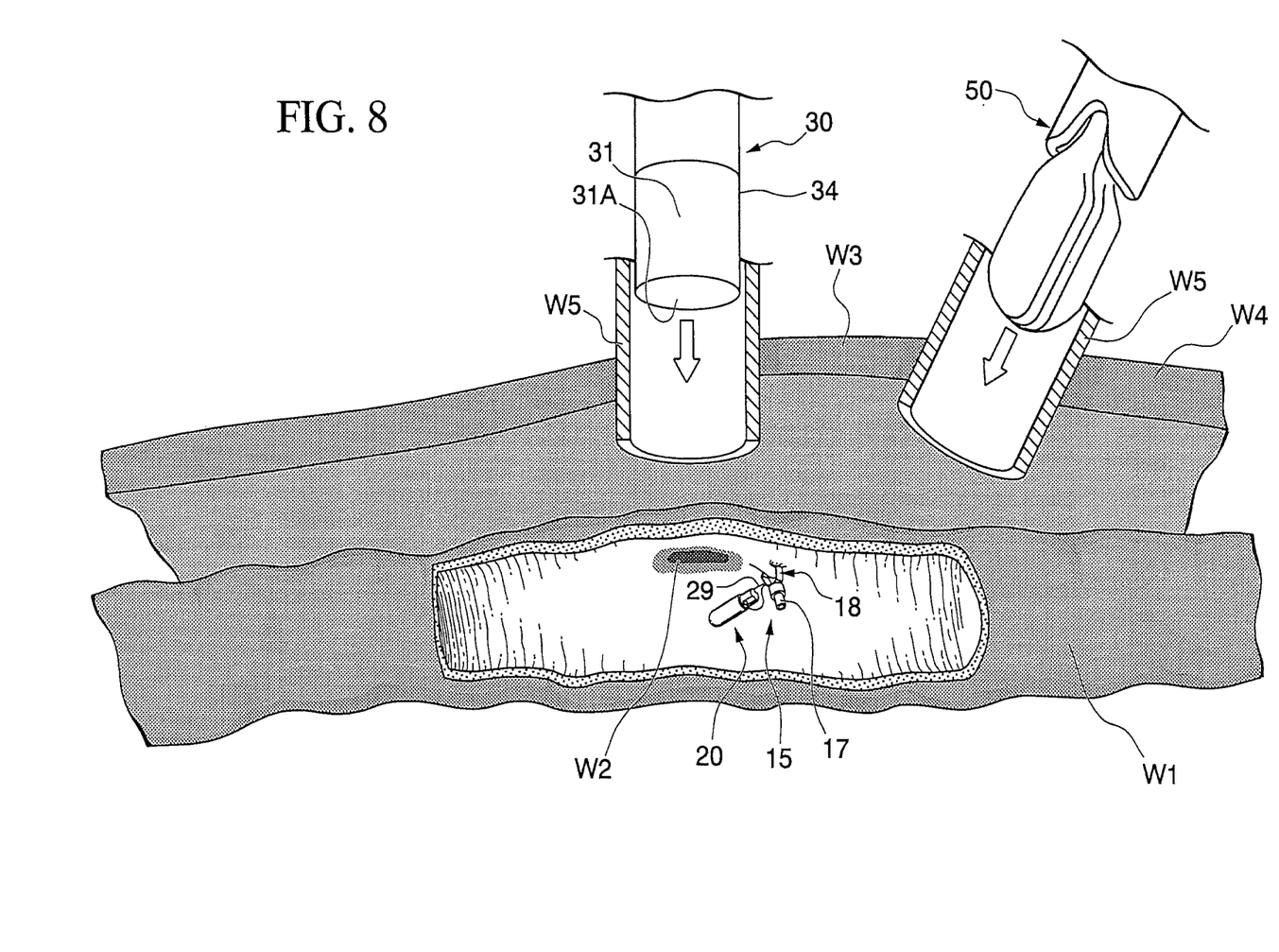
FIG. 8 is a diagram showing a step of inserting the magnetic forceps from an abdominal wall side.

After the indwelling tool 15 is anchored, the endoscope 41 is pulled out from the luminal organ W1. As shown in FIG. 8, two holes are formed in an abdominal wall W4, the positions of the holes being close to the diseased part W2, and a forceps port W5 is inserted into each hole.

Figure 9:
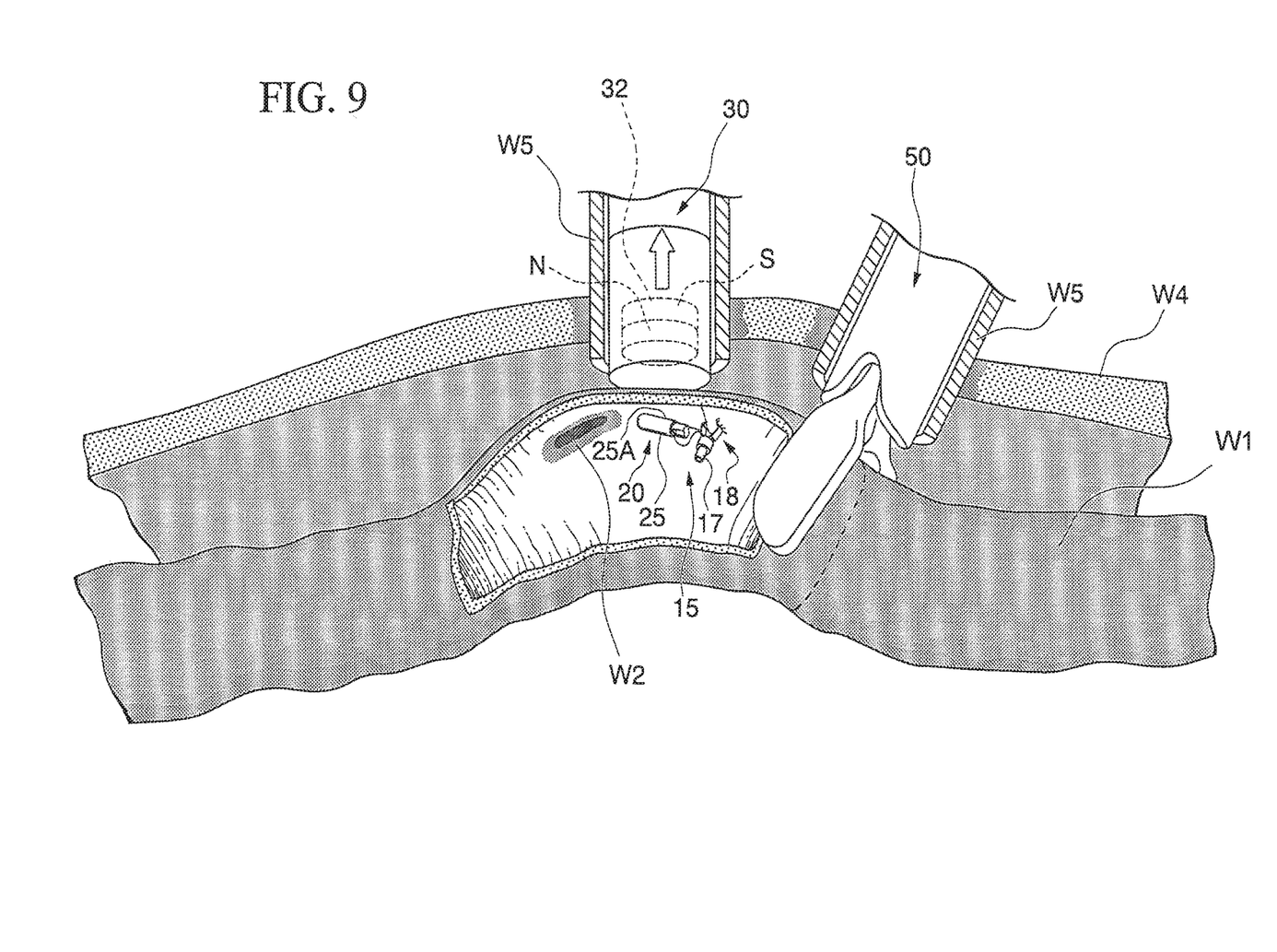
FIG. 9 is a diagram showing a state in which a tissue including a diseased part is lifted.
Figure 10:
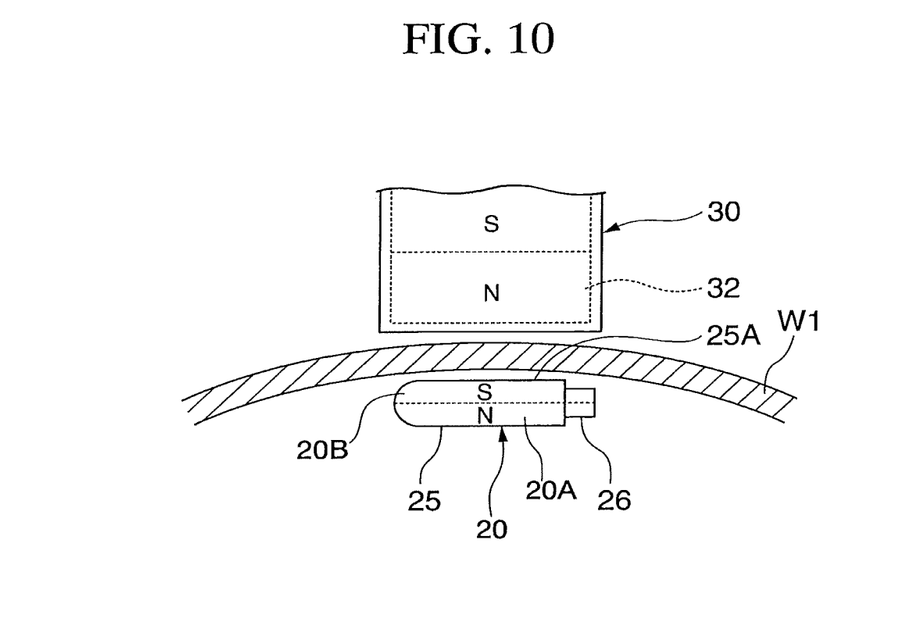
FIG. 10 is a diagram showing a state in which the magnetic body is attracted by the magnetic forceps.

The magnetic forceps 30 are inserted into the first forceps port W5, and cutting forceps 50 are inserted into the second forceps port W5. The lever 33A of the operation section 33 of the magnetic forceps 30 (see FIG. 4) is pulled so as to make the magnet 32 approach the cover 31A on the head side. As shown in FIG. 9, due to a magnetic field generated by the magnet 32 of the magnetic forceps 30, the magnetic body 20 is magnetized and is attracted so that the magnetic body 20 contacts an inner wall of the luminal organ W1 in a manner such that an outer peripheral face 25A as a side face of the main body 25 along the axis thereof faces the magnet 32. As shown in FIG. 10, when the magnetic forceps 30 are made to approach the luminal organ W1 from the outside thereof, the magnetic body 20 is directed in correspondence to the magnetic pole of the magnet 32 of the magnetic forceps 30. When the N pole of the magnetic forceps 30 faces the luminal organ W1, the side face 25A on the part 20B side (as the N pole) contacts the inner wall of the luminal organ W1.

Accordingly, the indwelling tool 15 moves toward the magnetic forceps 30. When the indwelling tool 15 is attracted to the magnetic forceps 30 and moves, a tissue (including the diseased part W2) in the vicinity of the indwelling tool 15 is also attracted toward the magnetic forceps 30. As a result, in the luminal organ W1, the tissue including the diseased part W2 protrudes toward the abdominal wall W4. In other words, the position of the tissue including the diseased part W2 is offset from its natural position toward the abdominal wall W4 (i.e., the tissue is lifted to the abdominal wall W4 side). The cutting forceps 50 are then inserted into the second forceps port W5, so as to cut a peripheral line (see a dashed line in FIG. 9) around the position of the indwelling tool 15 and to remove a bent portion of the luminal organ W1. The isolated tissue is extracted from the second forceps port W5, and the remaining parts of the luminal organ W1 are seamed together.

In the present embodiment, the indwelling tool 15 having the magnetic body 20 is made to indwell in the vicinity of the diseased part W2. Therefore, when the magnetic forceps 30 are made to approach from the outside of the luminal organ W1 so as to attract the magnetic body 20, a tissue including the diseased part W2 can be lifted toward the abdominal wall W4. Accordingly, it is possible to reliably isolate the diseased part W2 from the other tissues such as other luminal organs or other kinds of organs and to easily remove the diseased part W2. In addition, the magnetic body 20 is divided into two magnetized polar parts on either side of a plane parallel to the axis of the magnetic body 20; thus, the outer peripheral face 25A along the axis of the main body 25 contacts a tissue, so that a wide area can contact the tissue. Therefore, less burden is imposed on the tissue.

Second Embodiment

Figure 11:
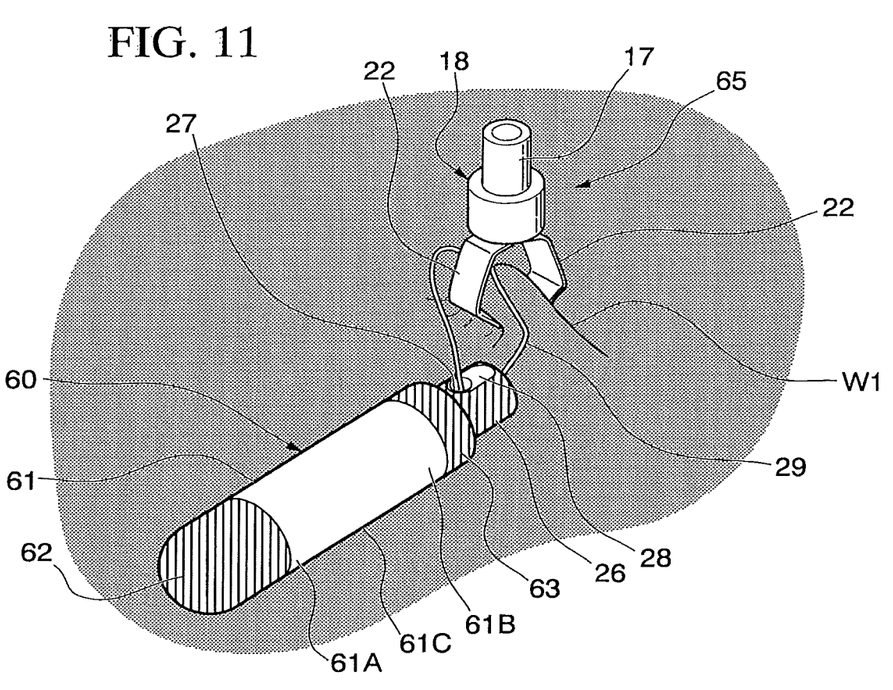
FIG. 11 is a diagram showing the structure of an indwelling tool.

FIG. 11 shows a magnetic body used in the present embodiment. A magnetic body unit 60 has a cylindrical main body 61 made of a soft magnetic material in the present embodiment, where a soft magnetic body (may also be called the soft magnetic material) is a magnetic body which loses its magnetic property when magnetic effects are excluded. That is, when being laid in a magnetic field, the soft magnetic body is magnetized, and when being extracted from the magnetic field (i.e., the magnetic field is removed), the soft magnetic body is substantially demagnetized. As a material for the soft magnetic body, iron, pure iron, silicon iron, Permalloy iron, or the like, are known.

The length along the axis of the main body 61 is sufficiently larger than the diameter of the main body 61. A first part 62 made of a non-magnetic material is fastened to an end 61A along the length of the main body 61. The first part 62 has the same outer diameter as that of the main body 61, and an end of the first part 62 has a spherical shape. To another end 61B of the main body 61 along the length thereof, a second part 63 made of a non-magnetic material is fastened. The second part 63 has the same outer diameter as that of the main body 61, and an end of the second part 63 forms the holding portion 26 having a smaller diameter. In the holding portion 26, the through hole 27 and the groove 28 are formed, through which the wire 29 passes. The first part 62 and the second part 63 may be made of rubber, resin, or the like.

The magnetic body unit 60, the wire 29, the clip 18, the tube 17, and the connection plate 16 form an indwelling tool 65 attached to the indwelling device 1. The outer diameter of the main body 61 is substantially the same as that of the insertion pipe 10. The holding portion 26 of the second part 63 can be loosely fit to the insertion pipe 10. When the indwelling tool 65 is attached to the indwelling device 1, the axis of the main body 61 coincides with the axis of the head portion of the indwelling device 1.

The operation of the present embodiment will be explained below.

The indwelling device 1 to which the indwelling tool 65 is attached is inserted through the working channel 44 of the endoscope 41 to the vicinity of the diseased part W2. In this process, the axis of the magnetic body unit 60 is arranged substantially parallel to the axis (i.e., the length) of the working channel 44 and the axis of the endoscope 41. When the wire 8 is withdrawn and the clip 18 of the indwelling tool 65 is anchored to a peripheral part of the diseased part W2, the magnetic forceps 30 are made to approach from the outside of the luminal organ W1, so that the main body 61 of the magnetic body unit 60 is magnetized due to the magnetic field produced by the magnetic forceps 30 and is attracted toward the magnetic forceps 30.

Figure 12:
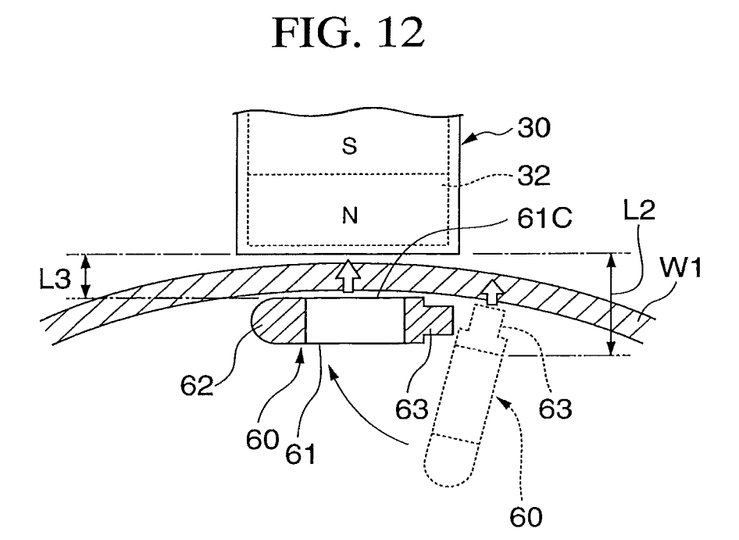
FIG. 12 is a diagram showing a state in which the magnetic body is attracted by the magnetic forceps.

As shown by dashed lines in FIG. 12, when the magnetic body unit 60 is arranged in a manner such that the second part 63 contacts an inner wall of the luminal organ W1 and the magnetic body unit 60 is erected on this contact point, the magnetic body unit 60 falls with respect to a fulcrum on the second part 63 side. The second part 63 is made of a non-magnetic material. Therefore, regarding the distance from the main body 61 of the magnetic body unit 60 to the magnet 32 of the magnetic forceps 30, a distance L3, measured when the magnetic body unit 60 is laid, that is, when an outer peripheral face 61C, which is a side face of the main body 61, faces the magnet 32, is less than a distance L2, measured when the magnetic body unit 60 is erected, that is, the axis of the magnetic forceps 30 is substantially in parallel to the axis of the magnetic body unit 60, thereby generating a strong attraction. Therefore, the magnetic body unit 60 is more stable when the outer peripheral face 61C of the main body 61 along the axis thereof faces the magnetic forceps 30. In accordance with this position, the outer peripheral face 61C of the main body 61 pushes against an inner wall of the luminal organ W1, so that a portion around a center point where the indwelling tool 65 is anchored is lifted. When the magnetic body unit 60 is erected on the first part 62 side, the magnetic body unit 60 falls with respect to a fulcrum on the first part 62 side, so that the outer peripheral face 61C of the main body 61 faces the magnet 32. The following steps in the operation are the same as those of the first embodiment.

In the present embodiment, both ends (i.e., the first part 62 and the second part 63) of the magnetic body unit 60 are each made of a non-magnetic material; thus, when the magnetic forceps 30 are made to approach, an inner wall of the luminal organ W1 can always be pushed by the outer peripheral face 61C of the main body 61. Here, the magnetic body unit 60 must be a long form so as to be inserted through the working channel 44. Therefore, in comparison with the area of either end of the magnetic body unit 60, the area of the outer peripheral face 61C is considerably larger. Accordingly, in comparison with a case in which either end of the magnetic body unit 60 closely contacts a tissue, a wider contact area can be secured when the outer peripheral face 61C contacts a tissue, so that the position of the magnetic body unit 60 can be stable in attraction using the magnetic forceps 30. In addition, less burden is imposed on the tissue pushed by the magnetic body unit 60, and the direction of the magnetic body unit 60 can coincide with that of the magnet 32.

Third Embodiment

Figure 13:
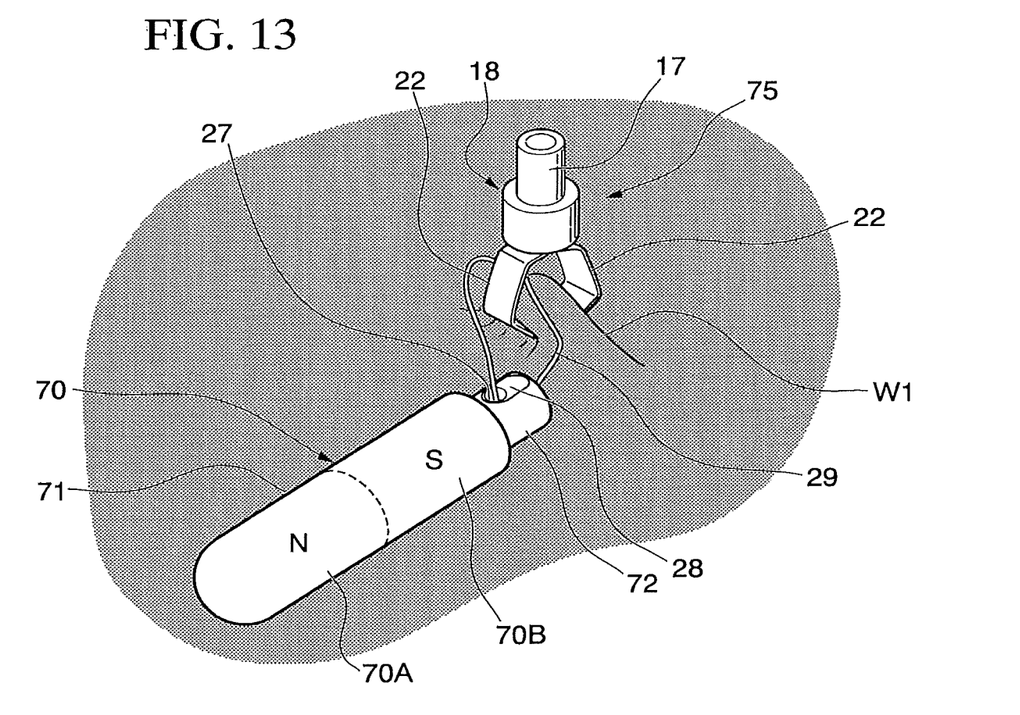
FIG. 13 is a diagram showing the structure of an indwelling tool.

FIG. 13 shows a magnetic body used in the present embodiment. A magnetic body 70 has a cylindrical shape and is made of a permanent magnet. The magnetic body 70 has a cylindrical main body 71 having a spherical head, and a holding portion 72 having a lesser diameter, formed on the base side of the main body 71. The axis along the length of the magnetic body 70 is sufficiently longer than the diameter of the main body 71. The main body 71 is divided into two magnetized polar parts with respect to a line perpendicular to the axis of the main body 71, the line being positioned near the center along the length of the main body 71: one is a part 70A as an N pole on the head side, and the other is a part 70B as an S pole on the base side.

The magnetic body 70, the wire 29, the clip 18, the tube 17, and the connection plate 16 form an indwelling tool 75 which is attached to the indwelling device 1. The outer diameter of the magnetic body 70 is substantially the same as that of the insertion pipe 10. The holding portion 72 can be loosely fit to the insertion pipe 10. When the indwelling tool 75 is attached to the indwelling device 1, the axis of the magnetic body 70 coincides with the axis of the head portion of the indwelling device 1.

Figure 14:
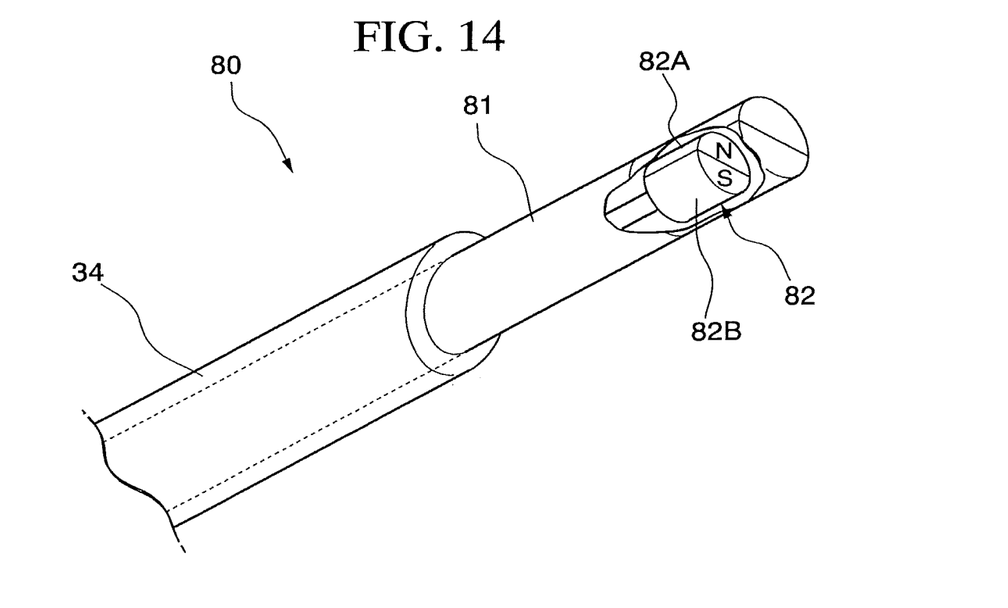
FIG. 14 is an enlarged and partially-broken view of a head portion of the magnetic forceps.

FIG. 14 shows magnetic forceps 80 as a magnetic field generating device used in the present embodiment. In the magnetic forceps 80, a magnet 82 is contained in an insertion portion 81 in a manner such that the magnet 82 can freely be advanced or withdrawn. The magnet 82 is divided into two magnetized polar parts which are arranged parallel along the length of the insertion portion 81: one is a part 82A as an N pole and the other is a part 82B as an S pole.

The operation of the present embodiment will be explained below.

The indwelling device 1 to which the indwelling tool 75 is attached is inserted through the working channel 44 of the endoscope 41 to the vicinity of the diseased part W2. In this process, the axis of the magnetic body 70 is arranged substantially parallel to the axis (i.e., the length) of the working channel 44 and the axis of the endoscope 41. When the clip 18 of the indwelling tool 75 is anchored to a peripheral part of the diseased part W2, the magnetic forceps 80 are made to approach from the outside of the luminal organ W1.

Figure 15:
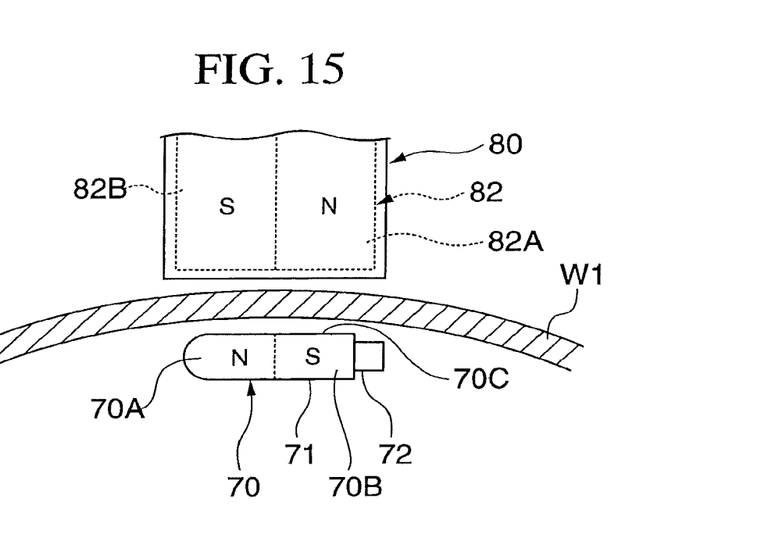
FIG. 15 is a diagram showing a state in which the magnetic body is attracted by the magnetic forceps.

Accordingly, the N pole of the magnet 82 of the magnetic forceps 80 is attracted to the part 70B (i.e., the S pole) of the magnetic body 70, and the S pole of the magnet 82 of the magnetic forceps 80 is attracted to the part 70A (i.e., the N pole) of the magnetic body 70. As shown in FIG. 15, in the magnetic body 70, a side face of the main body 71 along the axis of the magnetic body 70, that is, an outer peripheral face 71C contacts an inner plane of the luminal organ W1. The following steps are the same as those of the first embodiment.

In the present embodiment, the magnetic body 70 is divided into two magnetized polar parts which are arranged along the length of the magnetic body 70; thus, the outer peripheral face 71C of the main body 71 of the magnetic body 70 can be reliably attracted using the magnet 82. The magnetic body 70 must be a long shape so as to be inserted through the working channel 44; thus, the area of the outer peripheral face 71C is considerably larger than the area of either end of the magnetic body 70 along the length thereof. Therefore, in comparison with a case in which either end of the magnetic body 70 closely contacts a tissue, a wider contact area can be secured when the outer peripheral face 71C contacts a tissue. Accordingly, the position of the magnetic body 70 can be stable in attraction using the magnetic forceps 80. In addition, less burden is imposed on the tissue pushed by the magnetic body 70, and the direction of the magnetic body 70 can coincide with that of the magnet 82.

Fourth Embodiment

Figure 16:
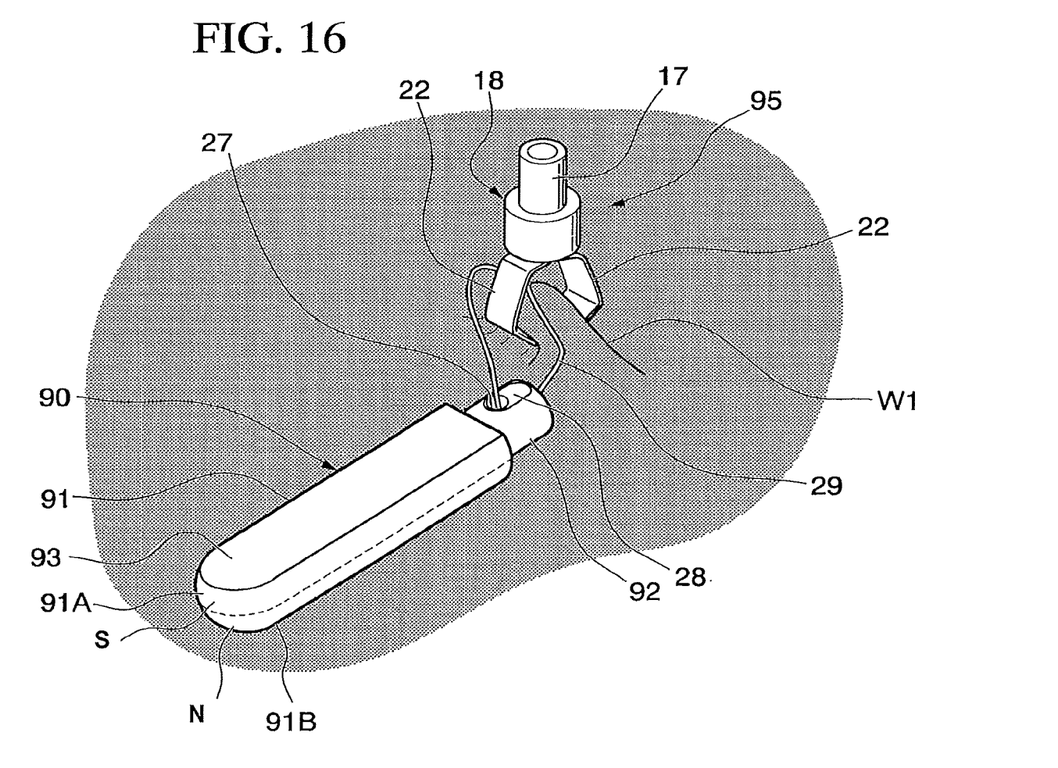
FIG. 16 is a diagram showing the structure of an indwelling tool.

FIG. 16 shows a magnetic body used in the present embodiment. A magnetic body 90 has a long main body 91 and a holding portion 92 extending from a base portion of the main body 91. The main body 91 has a plane 93 (i.e., a side face) parallel to the axis along the length of the main body, which is produced by cutting a part of a cylindrical shape. The head of the main body 91 has a spherical shape. The main body 91 is made of a permanent magnet and is divided into N and S polar parts which are arranged parallel to the plane 93. In FIG. 16, a part 91A on the plane 93 side is the N polar part, and a part 91B on the opposite side is the S polar part which includes no cut or removed part.

The magnetic body 90, the wire 29, the clip 18, the tube 17, and the connection plate 16 form an indwelling tool 95 which is attached to the indwelling device 1. The outer diameter of the main body 91 of the magnetic body 90 is substantially the same as that of the insertion pipe 10. The holding portion 92 can be loosely fit to the insertion pipe 10. When the indwelling tool 95 is attached to the indwelling device 1, the axis of the magnetic body 90 coincides with the axis of the head portion of the indwelling device 1.

The operation of the present embodiment will be explained below.

The indwelling device 1 to which the indwelling tool 95 is attached is inserted through the working channel 44 of the endoscope 41 to the vicinity of the diseased part W2. In this process, the axis of the magnetic body 90 is arranged substantially parallel to the axis of the working channel 44 and the axis of the endoscope 41. When the clip 18 of the indwelling tool 95 is anchored to a peripheral part of the diseased part W2, the magnetic forceps 30 are made to approach from the outside of the luminal organ W1.

Figure 17:
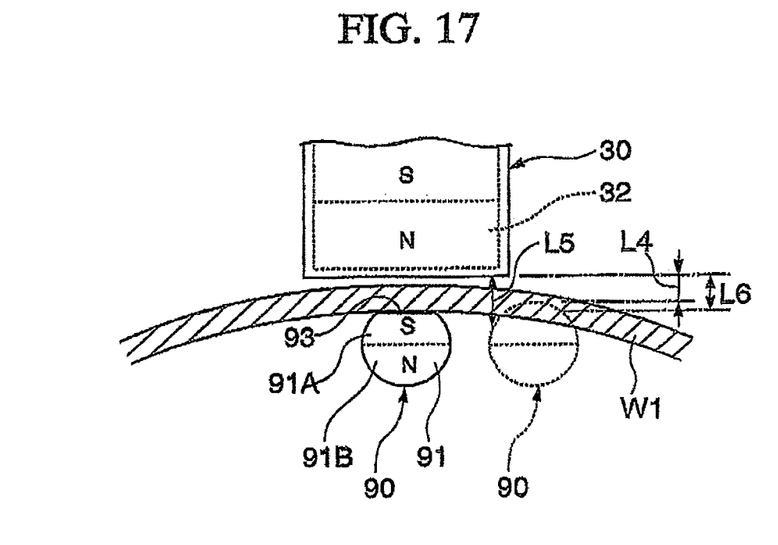
FIG. 17 is a diagram showing a state in which the magnetic body is attracted by the magnetic forceps.

As shown in FIG. 17, the magnetic body 90 is attracted in a manner such that the plane 93 (i.e., the S pole) faces the N pole of the magnet 32 of the magnetic forceps 30. As shown by imaginary lines, if the magnetic body has a circular section, the center part of the magnetic body, which is closer to the magnet 32 (refer to a distance L4), is attracted by a stronger magnetic force; however, the further the position from the center part, the more rapidly the distance to the magnet 32 (see a distance L5) increases and the attraction force decreases. In contrast, in the magnetic body 90, a wide area of the plane 93 closely contacts a tissue at a distance L6 which is shorter than the distance L5, so that a stable and large magnetic force is applied to the magnet 32. Therefore, in comparison with a case in which the magnetic body 90 has a circular section, a tissue (including the diseased part W2) around the indwelling tool 95 can be attracted toward the magnetic forceps 30 by a stronger attraction force and be lifted toward the abdominal wall W4. The following steps are the same as those of the first embodiment.

In the present embodiment, the plane 93 is provided in the magnetic body 90 having a long and cylindrical shape, which can be inserted into the working channel 44. Therefore, when the plane 93 is made to face the magnetic forceps 30, the plane 93 can closely contact the inside of the luminal organ W1. In this process, a wider area is attracted toward the magnet 32 in comparison with an end of the magnetic body 90; thus, the position of the magnetic body 90 can be stable. In addition, an area which contacts the tissue can be increased, thereby reducing a burden imposed on the tissue.

The present invention can be widely applied without being limited to the disclosed embodiments.

For example, the magnetic body may have a polygonal section formed perpendicularly to the axis thereof. The working channel 44 may be a channel attached to an outer periphery of the endoscope 41. A plurality of indwelling tools may be disposed around the diseased part W2 so that a magnetic body of each indwelling tool is attracted so as to lift a tissue including the diseased part W2.

The working channel 44 may not be integrally provided together with the endoscope 41. For example, while observation is performed using an observation device (e.g., a capsule endoscope) which can be swallowed, a working channel having no observation function may be introduced into a living body, so as to perform treatment as described above (the working channel may have an observation function; however, one having no observation function can be thinner, and a burden imposed on the patient can be much more reduced).

What is claimed is:

1. A method comprising:
providing an indwelling tool comprising a magnetic body and a clip connected with the magnetic body, within a luminal organ in an abdominal cavity of a body by:
inserting an endoscope into a lumen of the luminal organ;
identifying with the endoscope a part of an inner wall of the luminal organ, the part being positioned at a predetermined distance from a diseased part; and
inserting the indwelling tool through a working channel of the endoscope into the lumen of the luminal organ;
grasping the part of the inner wall of the luminal organ by the clip of the indwelling tool;
forming a first hole in an abdominal wall;
inserting magnetic forceps into the first hole and disposing a magnet of the magnetic forceps at an outside of the luminal organ and inside the abdominal wall;
moving the magnetic forceps inserted into the first hole closer to an outer wall of the luminal organ lying within a region that overlaps an outside of the luminal organ with respect to the diseased part in a transverse section of the luminal organ;
causing the luminal organ including the diseased part to bend in the abdominal cavity by retracting the magnet of the magnetic forceps from a vicinity of the outer wall toward the abdominal wall so that the luminal organ including the diseased part forms a bent portion, the magnet of the magnetic body keeping contact with the inner wall of the luminal organ by the magnetic force of the magnetic forceps while retracting the magnet of the magnetic forceps;
forming a second hole in the abdominal wall;
inserting cutting forceps into the second hole; and
excising the bent portion of the luminal organ including the diseased part in the abdominal cavity by the cutting forceps inserted into the second hole.

2. The method according to claim 1,
wherein the bent portion of the luminal organ including the diseased part is excised in the abdominal cavity by the cutting forceps inserted into the second hole while continuing to cause the bent portion to be formed by retracting the magnet of the magnetic forceps towards the abdominal wall.

* * * * *